United States Patent [19]

Shibata et al.

[11] Patent Number: 5,324,735
[45] Date of Patent: Jun. 28, 1994

[54] QUINOLINE CARBOXYLIC ACID DERIVATIVES

[75] Inventors: Akihiro Shibata, Yachiyo; Hideaki Matsuda, Abiko; Takemitsu Asaoka, Narita; Masaru Matsumoto, Tomisato; Ryuichi Kawahara, Ichikawa; Tatsuhiko Katori, Tone; Naokata Taido, Funabashi; Tadayuki Kuraishi, Chiba, all of Japan

[73] Assignee: SS Pharmaceutical Co., Ltd., Tokyo, Japan

[21] Appl. No.: 807,856
[22] PCT Filed: Mar. 29, 1990
[86] PCT No.: PCT/JP90/00425
§ 371 Date: Jan. 17, 1992
§ 102(e) Date: Jan. 17, 1992
[87] PCT Pub. No.: WO91/01308
PCT Pub. Date: Feb. 7, 1991

[30] Foreign Application Priority Data

Jul. 21, 1989 [JP] Japan .................. 1-189214

[51] Int. Cl.⁵ .................. C07D 215/233; A01K 31/47
[52] U.S. Cl. .................................. 514/312; 546/156
[58] Field of Search .................. 546/156; 514/312

[56] References Cited

U.S. PATENT DOCUMENTS

| | | | |
|---|---|---|---|
| 4,292,317 | 9/1981 | Pesson | 546/156 |
| 4,448,962 | 5/1984 | Irikura et al. | 546/156 |
| 4,530,930 | 7/1985 | Uno | 546/156 |
| 4,727,080 | 2/1988 | Soler | 546/156 |
| 4,894,458 | 1/1990 | Masuzawa | 546/156 |

FOREIGN PATENT DOCUMENTS

| | | |
|---|---|---|
| 50-106974 | 8/1975 | Japan . |
| 50-108276 | 8/1975 | Japan . |
| 5466686 | 5/1979 | Japan . |
| 56-30964 | 3/1981 | Japan . |
| 60-28964 | 2/1985 | Japan . |
| 61-189281 | 8/1986 | Japan . |
| 62-30776 | 2/1987 | Japan . |
| 62-207258 | 9/1987 | Japan . |
| 63-45261 | 2/1988 | Japan . |
| 63-179856 | 7/1988 | Japan . |
| 63-280068 | 11/1988 | Japan . |

OTHER PUBLICATIONS

Remuzon et al. J. Med. Chem. 34 (1). 1991. pp. 29–37.

(List continued on next page.)

Primary Examiner—Frederick E. Waddell
Assistant Examiner—Phyllis G. Spivack
Attorney, Agent, or Firm—Oblon, Spivak, McClelland, Maier & Neustadt

[57] ABSTRACT

The present invention relates to a quinolone carboxylic acid derivative represented by the following the formula (I),

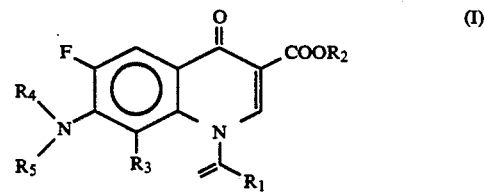

wherein $R_1$ is a lower alkyl group, $R_2$ is a hydrogen atom or a lower alkyl group, $R_3$ is a hydrogen atom or a halogen atom, $R_4$ and $R_5$ together form a five- or six-membered ring which may contain hetero atoms or may have substituents, provided that a compound wherein $R_1$ is a methyl group, $R_2$ and $R_3$ are hydrogen atom and

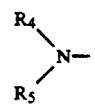

is a piperazinyl group is excluded; or a salt thereof; to an antimicrobial agent comprising the same as an effective component; and to an intermediate for producing same.

4 Claims, No Drawings

OTHER PUBLICATIONS

Journal of Medicinal Chemistry, vol. 32, 1989, pp. 537–542, D. Bouzard, et al., "Fluoronaphthyridines and Quinolones as Antibacterial Agents. 1. Synthesis and Structure-Activity Relationships of New 1-Substituted Derivatives".

Chemical Abstracts, vol. 109, 1988, pp. 381, 51554k, Y. Nishimura, et al., "Pyridonecarboxylic Acids as Antibacterial Agents. xxi. Synthesis and Antibacterial Activity of Enoxacin Analogs with a Variant at Position 1".

QUINOLINE CARBOXYLIC ACID DERIVATIVES

FIELD OF THE INVENTION

The present invention relates to a novel quinolone carboxylic acid derivative and a salt thereof which have excellent antimicrobial activity, to an antimicrobial agent comprising the same as an effective component, and to an intermediate for producing the same.

DESCRIPTION OF THE BACKGROUND

Synthetic antimicrobial agents such as nalidixic acid, piromidic acid, and the like are known as drugs for curing infectious diseases caused by Gram negative microorganisms. They exhibit, however, only deficient effects on intractable diseases such as pseudomoniasis and the like. On the other hand, antimicrobial agents with a stronger antimicrobial activity, such as norfloxacin, ofloxacin, and the like, have been developed and clinically used.

In order for an antimicrobial agent to effectively exhibit its action, the agent must have a strong antimicrobial activity and must be efficiently utilized. The above-mentioned conventional synthetic antimicrobial agents had a defect in that they are insufficiently absorbed, thus achieving only low utilization by living bodies.

In view of such a situation, the present inventors have synthesized a number of quinolone carboxylic acid derivatives and studied their antimicrobial activity and absorption efficiency by living bodies, and found that quinolone carboxylic acid derivatives of the following formula (I) and their salts exhibited excellent antimicrobial activities and superior absorptivity. Such a finding has led to the completion of the present invention.

DISCLOSURE OF THE INVENTION

An object of the present invention is to provide a quinolone carboxylic acid derivative having the following formula (I),

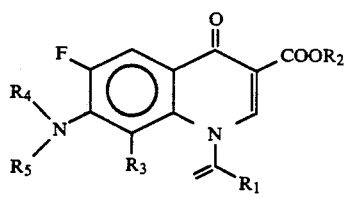

wherein $R_1$ is a lower alkyl group, $R_2$ is a hydrogen atom or a lower alkyl group, $R_3$ is a hydrogen atom or a halogen $R_4$ and $R_5$ together form a five- or six-membered ring which may contain hetero atoms or may have substituents, provided that a compound wherein $R_1$ is methyl group $R_2$ and $R_3$ are hydrogen atoms and

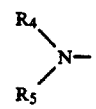

is a piperazinyl group is excluded; or a salt thereof; to an antimicrobial agent comprising the same as an effective component; and to an intermediate for producing the same.

In the present invention, groups represented by

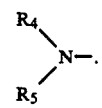

include piperazinyl, pyrrolidinyl, morpholino, and lower alkyl groups, hydroxy groups, amino groups, amino-lower-alkyl groups, are given as examples of the substituents.

In the present invention, an alkyl group is normally means a linear or branched alkyl group having 1-6 carbon atoms, specifically, methyl, ethyl, n-propyl, i-propyl, n-butyl, i-butyl, t-butyl, n-pentyl, n-hexyl, or the like. Examples given of halogen atoms are chlorine, bromine, iodine, fluorine.

The salts of the compounds of formula (I) of the present invention are not specifically limited so long as they are physiologically acceptable salts, and include salts of alkali metal, alkaline earth metal, inorganic acid, organic acid, and the like. Specific examples which can be given as salts of alkali metal are lithium salt, sodium salt, potassium salt, and the like; as salts of inorganic acids are hydrochloride, sulfate, nitrate, hydrobromide, phosphate, and the like; and as salts of organic acid are acetate, fumarate, maleate, lactate, citrate, tartrate malate, oxalate, methanesulfonate, benzenesulfonate, and the like.

The compounds of the present invention may have an asymmetric carbon atom depending the type of the group $$\begin{array}{c} R_4 \\ \diagdown \\ N-. \\ \diagup \\ R_5 \end{array}$$

The present invention include both the optical isomers and mixtures thereof.

The compound of formula (I) of the present invention can be prepared by one of the following processes.

<Process 1>

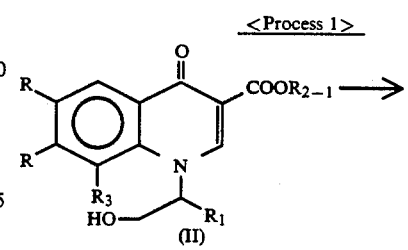

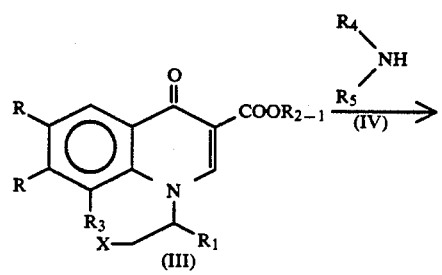

-continued
<Process 1>

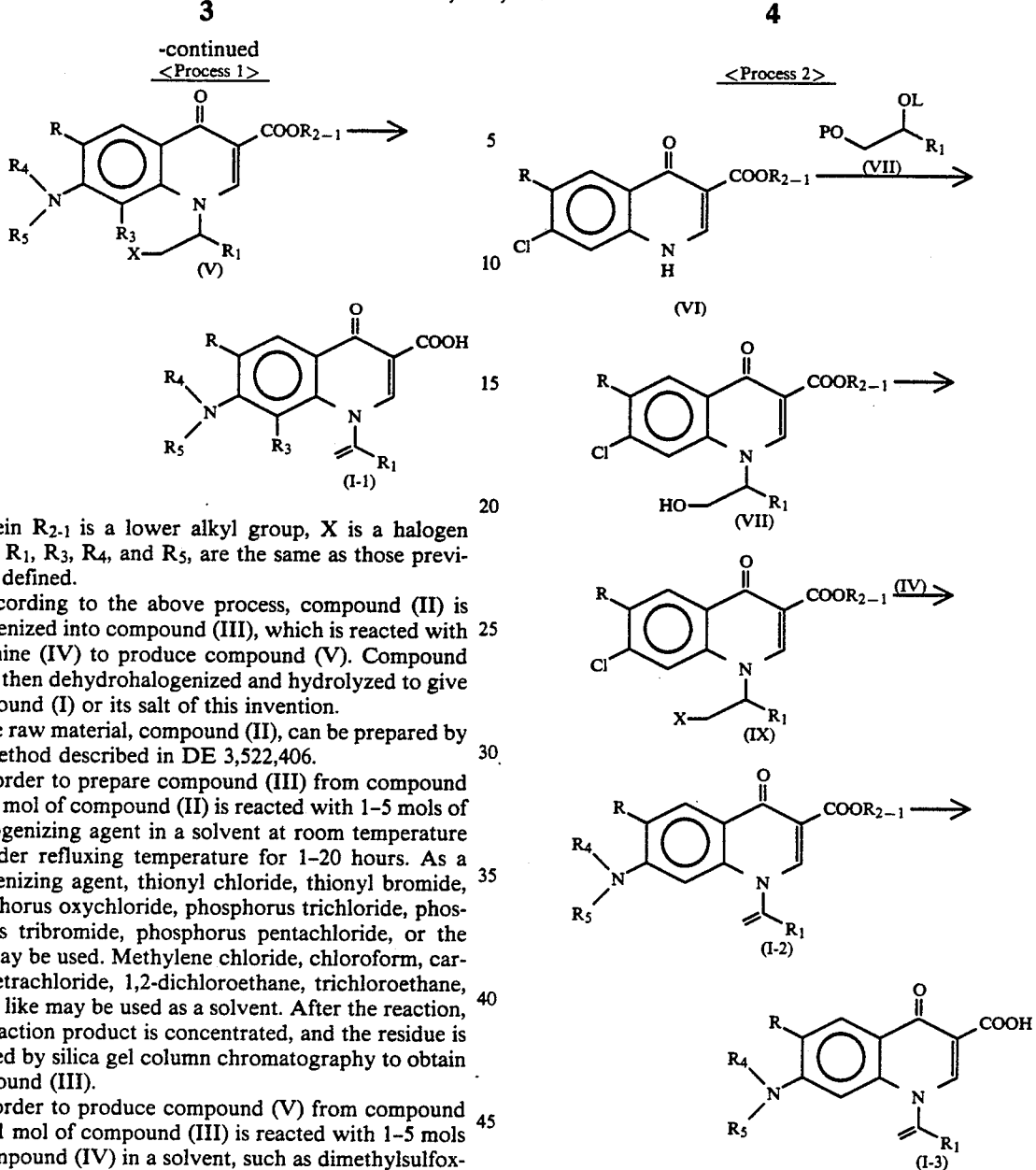

wherein $R_{2-1}$ is a lower alkyl group, X is a halogen atom, $R_1$, $R_3$, $R_4$, and $R_5$, are the same as those previously defined.

According to the above process, compound (II) is halogenized into compound (III), which is reacted with an amine (IV) to produce compound (V). Compound (V) is then dehydrohalogenized and hydrolyzed to give compound (I) or its salt of this invention.

The raw material, compound (II), can be prepared by the method described in DE 3,522,406.

In order to prepare compound (III) from compound (II), 1 mol of compound (II) is reacted with 1-5 mols of a halogenizing agent in a solvent at room temperature or under refluxing temperature for 1-20 hours. As a halogenizing agent, thionyl chloride, thionyl bromide, phosphorus oxychloride, phosphorus trichloride, phosphorus tribromide, phosphorus pentachloride, or the like may be used. Methylene chloride, chloroform, carbon tetrachloride, 1,2-dichloroethane, trichloroethane, or the like may be used as a solvent. After the reaction, the reaction product is concentrated, and the residue is purified by silica gel column chromatography to obtain compound (III).

In order to produce compound (V) from compound (III), 1 mol of compound (III) is reacted with 1-5 mols of compound (IV) in a solvent, such as dimethylsulfoxide, acetonitrile, or the like, at room temperature to 100° C. for 1-15 hours. After the reaction, the reaction mixture is poured into cold water, neutralized with an acid, and extracted with a solvent such as chloroform or the like. After evaporation of the solvent or after concentrating the reaction product, the residue is washed with water to obtain a crude product, which is purified by silica gel column chromatography or by the recrystallization to obtain compound (V).

For preparing compound (I-1) from compound (V), 1 mol of compound (V) is reacted with 2-4 moles of an alkali in a solvent such as ethanol or the like while heating for 5-60 hours, followed by an addition of water and a further reaction with heating for 1-20 hours. Sodium hydroxide or potassium hydroxide is preferably used as an alkali. After the reaction, the reaction product is poured into cold water, neutralized with an acid, and extracted with a solvent such as chloroform or the like. After evaporation of the solvent, the residue is recrystallized from a suitable solvent to obtain pure compound (I-1).

wherein P is a protective group, L is a leaving group, and $R_1$, $R_{2-1}$, $R_4$, and $R_5$, and X have the same meaning as previously defined.

According to the above process, compound (VI) is reacted with compound (VII), which is halogenized to produce compound (IX). Compound (XI) is then reacted with an amine (IV) to obtain compound (I-2). Compound (I-2) is further hydrolyzed into compound (I-3).

The raw material, compound (VI), is a known compound. It can be prepared, for example, by the method described in J. Med. Chem. 23, 1358 (1980). In order to prepare compound (VIII) from compound (VI), 1 mol of compound (VI) is reacted with 2-4 mols of alkaline carbonate in a solvent such as dimethylformamide or the like at room temperature or under refluxing temperature for 1-20 hours. After the reaction, the reaction product is concentrated, acidified with acetic acid or the like, warmed at 40°-80° C. for 1-5 hours, and concentrated. The residue is extracted with a solvent such as chloroform or the like and purified by silica gel column chromatography, and, if necessary, may be recrystallized, to obtain compound (VIII).

The reaction for the production of compound (IX) from compound (VIII) can be carried out in the same manner as the reaction for obtaining compound (III) from compound (II) in Process 1.

For producing compound (I-2) from compound (IX), 1 mole of compound (IX) is reacted with 1-5 mols of compound (IV) in a solvent, such as dimethylsulfoxide, acetonitrile, or the like, at room temperature to 100° C. for 1-60 hours. After the reaction, the reaction mixture is poured into cold water and extracted with a solvent such as chloroform or the like. The chloroform layer is reverse-extracted with an acid, the water layer is alkalinized and again extracted with chloroform or the like. After removal of solvent the residue is purified by silica gel column chromatography to obtain compound (I-2).

In the reaction for preparing compound (I-3) from compound (I-2), compound (I-2) is heated in the presence of an alkali such as sodium hydroxide, potassium hydroxide, or the like in an aqueous alcohol for 1-5 hours. After the reaction, the reaction product is neutralized with an acid, concentrated and extracted with a solvent such as alcohol or the like. After evaporation of the solvent, the residue is purified by the recrystallization or the like to obtain compound (I-3).

If necessary, compound (I) thus obtained is converted into a salt, such as a salt of alkali metal, alkaline earth metal, inorganic acid, organic acid, or the like, according to a conventional method.

When the compound thus produced is a racemate, the optical isomer can be obtained, if desired, for example, by reacting it with an optically active acid to form a diastereomer and by separating the optical isomer by recrystallization, chromatography, or the like means. If the optical isomer cannot be separated, the target optical isomer with a desired stereoscopic structure can be prepared by using an optically active raw material.

When compound (I) of this invention thus prepared is used as an antimicrobial agent, it is preferably orally administered at a dose of 200 to 800 mg per day or parenterally at a dose of 5 to 40 mg per day, depending on the weight, the age, the sex, the physical conditions, or the symptom of the patient or the manner of administration.

Compound (I) can be formed into various antimicrobial preparations, such as tablets, granules, powders, capsules, suspensions, injections, suppositories, or the like, according to conventional methods. When solid preparations are produced, compound (I) is mixed with excipients, and as required, with binders, disintegrators, lubricants, coloring agents, sweetening agents, flavoring agents, fillers, coating agents, sugar-coating agents, and the like, and formed into preparations such as tablets, granules, powders, capsules, suppositories, or the like according to known methods. When compound (I) is made into a preparation for injection, it is by dissolved, suspended, or emulsified into an aqueous medium such as distilled water, or made into powder which is dissolvable when it is injected. Intravenous, intraarterial, intraportal, intraperitoneal, subcutaneous, or intramuscular injection are applicable.

EXAMPLES

The present invention is hereinafter described in more detail by way of examples and test examples, which are not intended to be limiting thereof.

Reference Example 1

Ethyl 1-(1-chloroprop-2-yl)-6,7,8-trifluoro-1,4-dihydro-4-oxoquinoline-3-carboxylate 0.988 gm (3.0 mmol) of ethyl 6,7,8-trifluoro-1,4-dihydro-1-(1-hydroxyprop-2-yl)-4-oxoquinoline-3-carboxylate was dissolved into 50 ml of chloroform. To this was added 0.714 gm (6.0 mmol) of thionyl chloride and the mixture was reacted with heating under refluxing for 10 hours. The reaction mixture was concentrated under reduced pressure and the residue was purified by silica gel column chromatography (chloroform:methanol=100:1) to obtain 1.001 gm of colorless, needle-like crystals of ethyl 1-(1-chloroprop-2-yl)-6,7,8-trifluoro-1,4-dihydro-4-oxoquinoline-3-carboxylate.

mp 190°-191° C.

IR (KBr): 1730, 1618 cm$^{-1}$.

$^1$H-NMR (CDCl$_3$) δ ppm: 1.40(3H, t, J=7.2Hz), 1.77(3H, d, d, J=6.5, 1.8Hz), 3.89(2H, d, d, J=5.5, 1.8Hz), 4.31(2H, q, J=7.2Hz), 5.2-5.7(1H, m), 7.9-8.3(1H, m), 8.58(1H, s).

Example 1

Ethyl 7-(3-amino-1-pyrrolidinyl)-1-(1-chloroprop-2-yl)-6,8-difluoro-1,4-dihydro-4-oxoquinoline-3-carboxylate 174 mg (0.5 mmol) of ethyl 1-(1-chloroprop-2-yl)-6,7,8-trifluoro-1,4-dihydro-4-oxoquinoline-3-carboxylate was dissolved into 20 ml of acetonitrile. To this was added 215 mg (2.5 mmol) of 3-aminopyrrolidine and the mixture was reacted with heating under refluxing for 7 hours. The reaction mixture was concentrated under reduced pressure and the residue was purified by silica gel column chromatography (chloroform:methanol=100:1-20:1) to obtain 172 mg of light yellow crystals of ethyl 7-(3-amino-1-pyrrolidinyl)-1-(1-chloroprop-2-yl)-6,8-difluoro-1,4-dihydro-4-oxoquinoline-3-carboxylate (Compound No. 1).

Compound Nos. 2-18 shown in Table 1 were prepared in the same manner as in this example.

TABLE 1

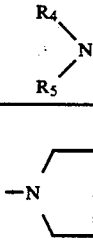

| Compound No. | $R_1$ | $R_{2-1}$ | $\begin{array}{c}R_4\\ \diagdown\\ N-\\ \diagup\\ R_5\end{array}$ | $R_3$ | X | Property mp (°C.) | IR cm$^{-1}$ (NaCl-film or KBr) | $^1$H-NMR ppm (CDCl$_3$) |
|---|---|---|---|---|---|---|---|---|
| 1 | CH$_3$ | C$_2$H$_5$ | 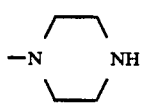 | F | Cl | light yellow crystals 106–108 | 3420, 3340, 1720, 1680 | 1.41(3H, t, J=7.2Hz), 1.70(2H, s), 1.73(2H, d, d, J=6.6, 1.5Hz), 1.8–2.3(2H, m), 3.2–4.1(7H, m), 4.39(2H, q, J=7.1Hz), 5.0–5.5(1H, m), 7.89(1H, d, d, J=14.1, 2.0Hz), 8.47(1H, s) |
| 2 | CH$_3$ | C$_2$H$_5$ | 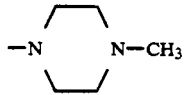 | F | Cl | light yellow oil | 3320, 1730, 1692 | 1.42(3H, t, J=7.2Hz), 1.77(3H, d, d, J=7.0, 1.8Hz), 2.20(1H, s), 2.8–3.5(8H, m), 3.90(2H, d, d, J=5.5, 3.0Hz), 4.41(2H, q, J=7.2Hz), 5.0–5.7(1H, m), 7.98(1H, d, d, J=12.5, 1.8Hz), 8.58(1H, s) |
| 3 | CH$_3$ | C$_2$H$_5$ | 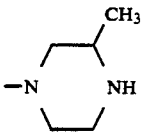 | F | Cl | light brown needlelike crystals 117–120 | 1728, 1692 | 1.39(3H, t, J=7.2Hz), 1.74(3H, d, J=6.5Hz), 2.83(3H, s), 2.4–2.8(4H, m), 3.2–3.6(4H, m), 3.87(2H, d, J=5.5Hz), 4.40(2H, q, J=7.2Hz), 5.1–5.8(1H, m), 7.97(1H, d, d, J=11.5, 1.8Hz), 8.53(1H, s) |
| 4 | CH$_3$ | C$_2$H$_5$ | 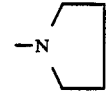 | F | Cl | light yellow-brown crystals 121–124 | 3490, 1727 1690 | 1.06(3H, d, J=5.7Hz), 1.42(3H, t, J=7.1Hz), 1.74(3H, d, d, J=1.8, 6.8Hz), 2.05(1H, s), 2.6–3.4(7H, m), 3.8–4.0(2H, m), 4.40(2H, q, J=7.2Hz), 5.2–5.4(1H, m) 7.97(1H, d, d, J=12.1, 1.9Hz), 8.52(1H, s) |
| 5 | CH$_3$ | C$_2$H$_5$ | 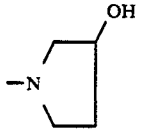 | F | Cl | light orange crystals 147–149 | 1720, 1690 | 1.41(3H, t, J=7.2Hz), 1.73(3H, d, d, J=6.7, 1.7Hz), 1.8–2.0(4H, m), 3.5–3.8(4H, m), 3.84(2H, d, d, J=5.8, 1.9Hz), 4.39(2H, q, J=7.2Hz), 5.1–5.6(1H, m), 7.88(1H, d, d, J=14.2, 2.0Hz), 8.47(1H, s) |
| 6 | CH$_3$ | C$_2$H$_5$ | 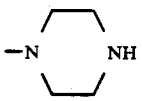 | F | Cl | light yellow crystals 177–180 | 3410, 1722 1612 | 1.40(3H, t, J=7.0Hz), 1.72(3H, br.d, J=6.9Hz), 1.8–2.2(2H, m), 2.95(1H, br.s), 3.4–4.2(6H, m), 4.38 (2H, q, J=7.0Hz), 4.4–4.6(1H, m), 5.1–5.5(1H, m), 7.75(1H, br.d, J=13.8Hz), 8.45, 8.47(1H, eachs) |
| 7 | C$_2$H$_5$ | C$_2$H$_5$ | 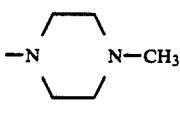 | F | Cl | light brown oil | 3310, 1724, 1690 | 1.02(3H, t, J=7.3Hz), 1.42(3H, t, 7.0Hz), 1.9–2.3(3H, m, 1H disappeared by D$_2$O), 2.8–3.1(4H, m), 3.1–3.4 (4H, m), 3.8–4.0(2H, d-like), 4.39(2H, q, J=7.0Hz), 4.9–5.11(1H, m), 7.98(1H, d, d, J=2.0, 12.1Hz), 8.49(1H, s) |
| 8 | C$_2$H$_5$ | C$_2$H$_5$ | 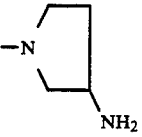 | F | Cl | light brown oil | 2945, 1724 1689 | 1.02(3H, t, J=7.3Hz), 1.42(3H, t, J=7.0Hz), 1.9–2.2 (2H, m), 2.37(3H, s), 2.4–2.7(4H, m), 3.2–3.5 (4H, m), 3.8–4.0(2H, d, d-like), 4.40(2H, q, J=7.0Hz), 4.9–5.4(1H, m), 7.98(1H, d, d, J=11.9, 1.8Hz), 8.48(1H, s) |
| 9 | C$_2$H$_5$ | C$_2$H$_5$ | 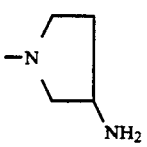 | F | Cl | light yellow needlelike crystals 115–119 | 3350, 1715 1612 | 1.00(3H, t, J=7.2Hz), 1.41(3H, t, J=7.0Hz), 1.64(2H, br.s. disappeared by D$_2$O), 1.6–2.3(4H, m), 3.2–4.0 (7H, m), 4.38(2H, q, J=7.2Hz), 4.8–5.2(1H, m), 7.89(1H, d, d, J=14.1, 1.8Hz), 8.44(1H, s) |
| 10 | CH$_3$ | C$_2$H$_5$ | (same as above) | H | Cl | light yellow-needlelike crystals 135–140 | 3430, 1718 1632 | 1.41(3H, t, J=7.1Hz), 1.67(2H, br.s), 1.75(3H, d, J=7.0Hz), 1.6–2.4(2H, m), 3.2–4.0(7H, m), 4.39(2H, q, J=7.1Hz), 4.6–5.1(1H, m), 6.35(1H, d, J=6.8Hz), 8.00(1H, d, J=14.4Hz), 8.44(1H, s) |

TABLE 1-continued

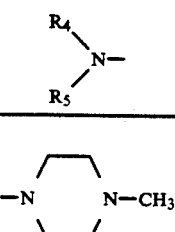

| Compound No. | $R_1$ | $R_{2-1}$ | 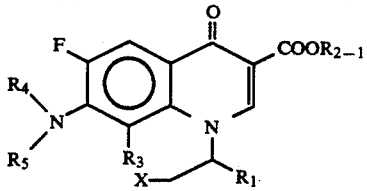 | $R_3$ | X | Property mp (°C.) | IR cm$^{-1}$ (NaCl-film or KBr) | $^1$H-NMR ppm (CDCl$_3$) |
|---|---|---|---|---|---|---|---|---|
| 11 | CH$_3$ | C$_2$H$_5$ | —N‾N—CH$_3$ (piperazinyl) | H | Cl | light brown needlelike crystals 156–159 | 2950, 1720 1612 | 1.41(3H, t, J=7.3Hz), 1.77(3H, d, J=6.6Hz), 2.38(3H, s), 2.4–2.7(4H, m), 3.1–3.4(4H, m), 3.84(2H, d, J=5.7Hz), 4.39(2H, q, J=7.3Hz), 4.7–5.1(1H, m), 6.82(1H, d, J=7.0Hz), 8.08(1H, d, J=13.2Hz), 8.50(1H, s) |
| 12 | CH$_3$ | C$_2$H$_5$ | —N‾NH with CH$_3$ | H | Cl | light brown amorphous 57–64 | 3425, 1720 1620 | 1.16(3H, d, J=6.6Hz), 1.41(3H, t, J=7.0Hz), 1.77(3H, d, J=6.6Hz), 2.19(1H, s, disappeared by D$_2$O), 2.3–3.2(5H, m), 3.3–3.6(2H, d-like), 3.85(2H, d, J=5.7Hz), 4.39(2H, q, J=7.0Hz), 4.7–5.1(1H, m), 6.82(1H, d, J=6.6Hz), 8.08(1H, d, J=13.2Hz), 8.50(1H, s) |
| 13 | CH$_3$ | C$_2$H$_5$ | —N (pyrrolidinyl) | H | Cl | light brown crystals 196–199 | 3425, 1712, 1626 | 1.41(3H, t, J=7.0Hz), 1.76(3H, d, J=6.2Hz), 1.9–2.2 (4H, m), 3.4–3.7(4H, m), 3.83(2H, d, J=5.3Hz), 4.38(2H, q, J=7.0Hz), 4.6–5.1(1H, m), 6.35(1H, d, J=7.5Hz), 7.99(1H, d, J=14.5Hz), 8.43(1H, s) |
| 14 | C$_2$H$_5$ | C$_2$H$_5$ | —N with NH$_2$ | H | Cl | light brown crystals 147–155 (dec) | 3425, 1715 1628 | 0.98(3H, t, J=7.3Hz), 1.39(3H, t, J=7.0Hz), 1.6–2.5 (6H, m, 2H disappeared by D$_2$O), 3.2–3.8(5H, m), 3.86(2H, d, J=5.7Hz), 4.37(2H, q, J=7.0Hz), 4.5–4.8 (1H, m), 6.37(1H, d, J=6.6Hz), 7.94(1H, d, J=14.5Hz), 8.37(1H, s) |
| 15 | C$_2$H$_5$ | C$_2$H$_5$ | —N‾N—CH$_3$ | H | Cl | light brown amorphous 68–73 | 3450, 1720 1620 | 0.99(3H, t, J=7.3Hz), 1.42(3H, t, J=7.0Hz), 1.9–2.25 (2H, m), 2.39(3H, s), 2.5–2.8(4H, m), 3.2–3.4(4H, m), 3.89(2H, d, J=6.6Hz), 4.40(2H, q, J=7.0Hz), 4.6–4.8(1H, m), 6.85(1H, d, J=6.6Hz), 8.10 (1H, d, J=13.2Hz), 8.45(1H, s) |
| 16 | C$_2$H$_5$ | C$_2$H$_5$ | —N‾NH | H | Cl | light brown amorphous 88–94 | 3420, 1717 1615 | 1.00(3H, t, J=7.3Hz), 1.42(3H, t, J=7.1Hz), 1.8–2.3 (2H, m), 2.40(1H, br.s), 3.0–3.4(8H, m), 3.89(2H, d, J=6.2Hz), 4.40(2H, q, J=7.1Hz), 4.5–4.9(1H, m), 6.86(1H, d, J=7.0Hz), 8.10(1H, d, J=13.2Hz), 8.45(1H, s) |
| 17 | C$_2$H$_5$ | C$_2$H$_5$ | —N‾NH with CH$_3$ | H | Cl | brown amorphous 64–69 | 3430, 1720 1615 | 0.99(3H, t, J=7.3Hz), 1.17(3H, d, J=6.6Hz), 1.42(3H, t, J=7.0Hz), 1.9–2.3(3H, m), 2.3–2.7(1H, m), 2.7–3.3 (4H, m), 3.3–3.8(2H, m), 3.89(2H, d, J=5.7Hz), 4.40(2H, q, J=7.0Hz), 4.5–4.9(1H, m), 6.84(1H, d, J=6.6Hz), 8.10(1H, d, J=13.6Hz), 8.45(1H, s) |
| 18 | C$_2$H$_5$ | C$_2$H$_5$ | —N (pyrrolidinyl) | H | Cl | brown crystals 165–170 | 3500, 1720 1610 | 0.98(3H, t, J=7.3Hz), 1.42(3H, t, J=7.2Hz), 1.8–2.6 (6H, m), 3.3–3.7(4H, m), 3.86(2H, d, J=5.7Hz), 4.39(2H, q, J=7.2Hz), 4.5–4.8(1H, m), 6.39(1H, d, J=7.0Hz), 8.03(1H, d, J=14.5Hz), 8.38(1H, s) |

Example 2

7-(3-Amino-1-pyrrolidinyl)-6,8-difluoro-1,4-dihydro-4-oxo-1-(prop-1-en-2-yl)-quinoline-3-carboxylic acid 159 mg (0.38 mmol) of ethyl 7-(3-amino-1-pyrrolidinyl)-1-(1-chloroprop-2-yl)-6,8-difluoro-1,4-dihydro-4-oxoquinoline-3-carboxylate (Compound No.1) prepared in Example 1 was dissolved into 20 ml of ethanol. To this was added 65 mg (1.15 mmol) of pulverized potassium hydroxide and the mixture was heated under refluxing for 14 hours. 3 ml of water was added and the mixture was heated under refluxing for a further 3 hours. After cooling, the reaction mixture was concentrated under reduced pressure, the residue was washed with water, and dried to obtain a crude product. The crude product was purified by silica gel column chromatography (chloroform:methanol=5:1) to obtain 52 mg of light yellow crystals of 7-(3-amino-1-pyrrolidinyl)-6,8-difluoro-1,4-dihydro-4-oxo-1-(prop-1-en-2-yl)-quinoline-3-carboxylic acid (Compound No. 19).

Compound Nos. 20–36 shown in Table 2 were prepared in the same manner as in this example.

TABLE 2

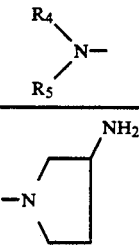

| Compound No. | R₁ | R₂ | R₄\N—\R₅ | R₃ | Property mp (°C.) | IR cm⁻¹ (KBr) | ¹H-NMR ppm (CDCl₃) |
|---|---|---|---|---|---|---|---|
| 19 | CH₃ | H | 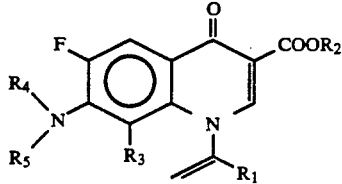 | F | light yellow crystals 174–178 (dec) | 3400, 1720, 1610 | 1.5–2.2(2H, m), 2.20(3H, s), 3.0–4.0(7H, m), 5.40 (2H, br), 7.60(1H, br.d), 8.41(1H, s) |
| 20 | CH₃ | H | 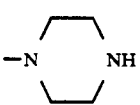 | F | light yellow-brown crystals 188–192 (dec) | 3420, 1720, 1620 | 2.23(3H, s), 2.9–3.2(4H, s), 3.2–3.5(4H, m), 5.29 (1H, s), 5.40(1H, s), 7.94(1H, d, d, J=11.9, 2.0Hz), 8.55(1H, s) |
| 21 | CH₃ | H | 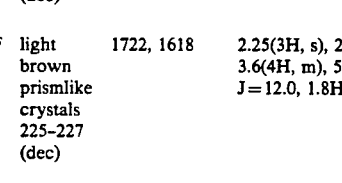 | F | light brown prismlike crystals 225–227 (dec) | 1722, 1618 | 2.25(3H, s), 2.40(3H, s), 2.5–2.8(4H, m), 3.3–3.6(4H, m), 5.32(1H, s), 5.39(1H, s), 7.88(1H, d, d, J=12.0, 1.8Hz), 8.52(1H, s) |
| 22 | CH₃ | H | 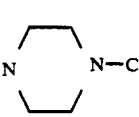 | F | light yellow crystals 181–184 (dec) | 3425, 1720, 1612 | 1.11(3H, d, J=5.5Hz), 2.22(3H, s), 2.7–3.5(8H, m) 5.28(1H, s), 5.37(1H, s), 5.5–6.7(1H, br), 7.91 (1H, d, d, J=11.9, 2.0Hz), 8.52(1H, s) |
| 23 | CH₃ | H | 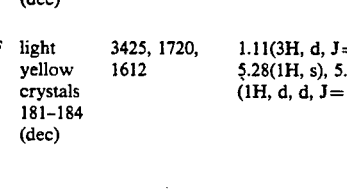 | F | light yellow needle-like crystals 251–253 (dec) | 1722, 1620 | 1.5–2.1(5H, m), 2.20(3H, s), 3.6–4.0(4H, m), 5.27 (1H, s), 5.32(1H, s), 7.81(1H, d, d, J=13.9, 1.9Hz), 8.48(1H, s) |
| 24 | CH₃ | H | 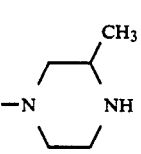 | F | light yellow prismlike crystals 251–252 (dec) | 3450, 1710, 1622 | 1.6–2.2(3H, m), 2.20(3H, s), 3.4–4.2(4H, m), 4.4–4.7(1H, m), 5.27(1H, s), 5.32(1H, s), 7.80(1H, d, d, J=13.9, 2.0Hz), 8.45(1H, s) |
| 25 | C₂H₅ | H | 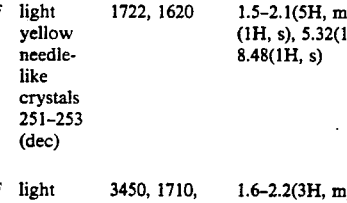 | F | white powderly crystal 229–234 (dec) | 3380, 1720, 1700 | 1.10(3H, t, J=7.4Hz), 2.3–2.7(2H, q-like), 2.7–3.4(6H, m), 3.4–3.7(4H, m), 5.46(1H, s), 5.52(1H s), 7.88(1H, d, d, J=11.9, 2.0Hz), 8.48(1H, s) |
| 26 | C₂H₅ | H | 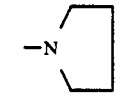 | F | light yellow powdery crystal 232–240 (dec) | 3425, 1718, 1606 | 1.10(3H, t, J=7.4Hz), 2.3–2.7(2H, q-like), 2.78 (3H, s), 2.9–3.4(5H, m), 3.5–3.8(4H, m), 5.46(1H, s), 5.52(1H, s), 7.89(1H, d, d, J=11.9, 2.0Hz), 8.48 (1H, s) |

TABLE 2-continued

Structure: quinoline core with F at 6-position, COOR$_2$ at 3-position, 4-oxo, R$_4$R$_5$N- at 7-position, R$_3$ at 8-position, R$_1$ at N-1 (with vinyl group).

| Compound No. | R$_1$ | R$_2$ | R$_4$R$_5$N- | R$_3$ | Property mp (°C.) | IR cm$^{-1}$ (KBr) | $^1$H-NMR ppm (CDCl$_3$) |
|---|---|---|---|---|---|---|---|
| 27 | C$_2$H$_5$ | H | 3-aminopyrrolidin-1-yl | F | light yellow powderlye crystals 217–222 (dec) | 3430, 1700, 1620 | 1.08(3H, t, J=7.4Hz), 1.8–2.3(2H, m), 2.3–2.6(2H, m), 2.8–4.6(7H, m), 5.42(1H, s), 5.49(1H, s), 7.77(1H, d, d, J=14.0, 1.9Hz), 8.40(1H, s) |
| 28 | CH$_3$ | H | 3-aminopyrrolidin-1-yl | H | light brown powderly crystal 221–225 (dec) | 3420, 1690, 1632 | 1.6–2.4(2H, m), 2.24(3H, s), 3.0–4.1(5H, m) 5.54(1H, s), 5.74(1H, s), 6.47(1H, d, J=7.5Hz) 7.85(1H, d, J=14.1Hz), 8.57(3H, s, 2H disappeared by D$_2$O) |
| 29 | CH$_3$ | H | 4-methylpiperazin-1-yl | H | light yellow-brown powderly crystal 240–244 (dec) | 3425, 1722, 1624 | 2.25(6H, s), 2.4–2.6(4H, m), 2.6–3.6(5H, m), 5.55(1H, s), 5.73(1H, s), 6.90(1H, d, J=7.4Hz), 7.87(1H, d, J=13.5Hz), 8.61(1H, s) |
| 30 | CH$_3$ | H | 3-methylpiperazin-1-yl | H | light brown powderly crystal 212–217 (dec) | 3450, 1720, 1622 | 1.30(3H, d, J=5.9Hz), 2.25(3H, s), 2.8–3.8(7H, m), 4.0–5.4(1H, br), 5.56(1H, s), 5.75(1H, s), 6.95(1H, d, J=7.2Hz), 7.91(1H, d, J=13.3Hz), 8.63(1H, s) |
| 31 | CH$_3$ | H | pyrrolidin-1-yl | H | light brown powderly crystal 276–281 (dec) | 2960, 1720, 1624 | 1.8–2.1(4H, m), 2.22(3H, s), 3.4–3.6(4H, m), 5.50(1H, s), 5.69(1H, s), 6.47(1H, d, J=7.9Hz), 7.81(1H, d, J=14.4Hz), 8.51(1H, s) |
| 32 | C$_2$H$_5$ | H | 3-aminopyrrolidin-1-yl | H | light brown powderly crystal 178–184 (dec) | 3425, 1720, 1710 | 1.09(3H, t, J=7.3Hz), 2.0–2.3(2H, m), 2.4–2.7(2H, m), 2.8–4.0(9H, m), 5.60(1H, s), 5.72(1H, s), 6.43(1H, d, J=7.7Hz), 7.85(1H, d, J=14.3Hz), 8.52(1H, s) |
| 33 | C$_2$H$_5$ | H | 4-methylpiperazin-1-yl | H | light brown powderly crystal 211–213 (dec) | 3440, 1720, 1620 | 1.09(3H, t, J=7.3Hz), 2.24(3H, s), 2.3–2.6(6H, m), 3.1–3.4(5H, m), 5.63(1H, s), 5.73(1H, s), 6.87(1H, d, J=7.5Hz), 7.91(1H, d, J=13.4Hz), 8.60(1H, s) |
| 34 | C$_2$H$_5$ | H | piperazin-1-yl | H | light yellow powderly crystal 164–170 (dec) | 3425, 1720, 1624 | 1.10(3H, t, J=7.3Hz), 2.2–2.7(2H, q-like), 3.0–3.7(10H, m), 5.64(1H, s), 5.74(1H, s), 6.91(1H, d, J=7.5Hz), 7.96(1H, d, J=13.2Hz), 8.62(1H, s) |
| 35 | C$_2$H$_5$ | H | 3-methylpiperazin-1-yl | H | light yellow powderly crystal 232–238 (dec) | 3425, 1730, 1624 | 1.10(3H, t, J=7.2Hz), 1.34(3H, d, J=5.3Hz), 2.3–2.7(3H, m), 2.8–3.8(8H, m), 5.64(1H, s), 5.76(1H, s), 6.91(1H, d, J=7.0Hz), 7.96(1H, d, J=13.0Hz), 8.62(1H, s) |

TABLE 2-continued

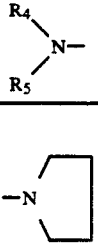

| Compound No. | R₁ | R₂ | R₄\N—\R₅ | R₃ | Property mp (°C.) | IR cm⁻¹ (KBr) | ¹H-NMR ppm (CDCl₃) |
|---|---|---|---|---|---|---|---|
| 36 | C₂H₅ | H | —N⟨pyrrolidinyl⟩ | H | light brown powderly crystal 213–220 (dec) | 3430, 1715, 1628 | 1.09(3H, t, J=7.3Hz), 1.8–2.0(4H, m), 2.3–2.7 (2H, q-like), 3.27(1H, s), 3.4–3.6(4H, m), 5.58(1H, s), 5.70(1H, s), 6.39(1H, d, J=7.7Hz), 7.77(1H, d, J=14.5Hz), 8.48(1H, s) |

Reference Example 2

Ethyl 7-chloro-6-fluoro-1,4-dihydro-1-(1-hydroxyprop-2-yl)-4-oxoquinoline-3-carboxylate 4.11 gm (15.3 mmol) of ethyl 7-chloro-6-fluoro-1,4-dihydro-4-oxoquinoline-3-carboxylate and 6.32 gm (45.7 mmol) of potassium carbonate anhydride were suspended into 80 ml of N,N-dimethylformamide. To this suspension was added dropwise 20 ml of a solution of 10.90 gm (45.7 mmol) of 1-(tetrahydro-2-pyranyloxy)-2-(methanesulfonyl)propane dissolved in N,N-dimethylformamide with heating at 120° C., and the mixture was stirred vigorously at 120° C. for 10 hours. The reaction mixture was filtered, and the filtrate was concentrated under reduced pressure, and 50 ml of acetic acid and 10 ml of water were added to the residue to effect the hydrolysis at 60° C. for 2 hours. The reaction product was filtered and the filtrate was concentrated. The residue was extracted with chloroform, followed by evaporation of chloroform. The residue thus obtained was purified by silica gel column chromatography (chloroform:methanol=20:1) and recrystallized with a small amount of chloroform to obtain colorless needlelike crystals of ethyl 7-chloro-6-fluoro-1,4-dihydro-1-(1-hydroxyprop-2-yl)-4-oxoquinoline-3-carboxylate.

mp: 238°–239° C.

IR (KBr): 3380, 1723, 1612 cm⁻¹.

¹H-NMR (CDCl₃) δ ppm: 1.36(3H, t, J=7.1Hz), 1.65(3H, d, J=6.8Hz), 2.4–2.8 (1H,br), 3.8–4.2(4H, m), 4.6–5.0(1H, m), 7.51(1H, d, J=9.2Hz), 7.76(1H, d, J=5.9Hz), 8.57(1H, s).

Reference Example 3

Ethyl 7-chloro-1-(1-chloroprop-2-yl)-6-fluoro-1,4-dihydro-4-oxoquinoline-3-carboxylate 7-chloro-6-fluoro-1,4-dihydro-1-(1-hydroxyprop-2-yl)-4-oxoquinoline-3-carboxylate obtained in Reference Example 2 was treated in the same manner as in Reference Example 1 to produce colorless prismlike crystals of ethyl 7-chloro-1-(1-chloroprop-2-yl)-6-fluoro-1,4-dihydro-4-oxoquinoline-3-carboxylate:

mp: 151°–153° C.

IR (KBr): 1725, 1612 cm⁻¹.

¹H-NMR (CDCl₃) δ ppm: 1.42(3H, t, J=7.1Hz), 1.78(3H, d, J=6.8Hz), 3.88(2H, d, J=5.7Hz), 4.41(2H, q, J=7.1Hz), 4.8–5.2(1H, q, like), 7.64(1H, d, J=5.5Hz), 8.27(1H, d, J=9.0Hz), 8.56(1H, s).

Example 3

Ethyl 6-fluoro-7-(4-methyl-1-piperazinyl)-1-(prop-1-en-2-yl)-1,4-dihydro-4-oxoquinoline-3-carboxylate Ethyl 7-chloro-1-(1-chloroprop-2-yl)-6-fluoro-1,4-dihydro-4-oxoquinoline-3-carboxylate obtained in Reference Example 3 was treated in the same manner as in Example 1 to produce light yellow crystals of ethyl 6-fluoro-7-(4-methyl-1-piperazinyl)-1-(prop-1-en-2-yl)-1,4-dihydro-4 -oxoquinoline-3-carboxylate (Compound No. 37).

The Compound Nos.38–42 in Table 3 were obtained in the same manner as in this Example.

TABLE 3

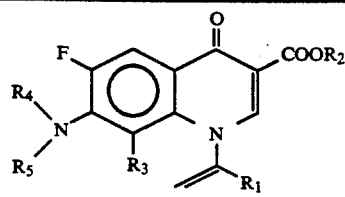

| Compound No. | R1 | R2 | R4\N—\R5 | R3 | Property mp (°C.) | IR cm$^{-1}$ (KBr) | $^1$H-NMR ppm (DMSO-d$_6$) |
|---|---|---|---|---|---|---|---|
| 37 | CH$_3$ | C$_2$H$_5$ | —N(CH$_2$CH$_2$)$_2$N—CH$_3$ | H | colourless needlelike crystals 204–207 | 2950, 1682, 1617 | 1.41(3H, t, J=7.0Hz), 2.21(3H, s), 2.39(3H, s), 2.4–2.7(4H, m), 3.1–3.4(4H, m), 4.39(2H, q, J=7.1Hz), 5.40(1H, s), 5.59(1H, s), 6.69(1H, d, J=7.0Hz), 8.04 (1H, d, J=13.2Hz), 8.34(1H, s) |
| 38 | CH$_3$ | C$_2$H$_5$ | —N(CH$_2$CH$_2$)$_2$NH | H | light yellow crystals 180–182 (dec) | 3430, 1705, 1615 | 1.41(3H, t, J=7.1Hz), 2.22(4H, s), 3.0–3.4(8H, m), 4.39(2H, q, J=7.1Hz), 5.51(2H, d, J=16.7Hz), 6.70 (1H, d, J=7.0Hz), 8.04(1H, d, J=13.4Hz), 8.35(1H, s) |
| 39 | CH$_3$ | C$_2$H$_5$ | —N(CH$_2$CH(CH$_3$)CH$_2$)NH (2-methylpiperazinyl) | H | light brown crystals 144–147 | 3425, 1724, 1615 | 1.14(3H, d, J=6.2Hz), 1.41(3H, t, J=7.3Hz), 1.9–2.2(1H, br), 2.22(3H, s), 2.2–3.2(5H, m), 3.2–3.6(2H, d-like), 4.38(2H, q, J=7.3Hz), 5.42(1H, s), 5.60(1H, s), 6.68(1H, d, J=7.0Hz), 8.03(1H, d, J=13.6 Hz), 8.34(1H, s) |
| 40 | C$_2$H$_5$ | C$_2$H$_5$ | —N(CH$_2$CH$_2$)$_2$N—CH$_3$ | H | brown crystals 123–125 | 3420, 1720, 1615 | 1.16(3H, t, J=7.4Hz), 1.41(3H, t, J=7.1Hz), 2.37(3H, s), 2.4–2.8(6H, m), 3.1–3.4(4H, m), 4.38(2H, q, J=7.1Hz), 5.46(1H, s), 5.61(1H, s), 6.67(1H, d, J=7.0 Hz), 8.03(1H, d, J=13.4Hz), 8.32(1H, s) |
| 41 | C$_2$H$_5$ | C$_2$H$_5$ | —N(CH$_2$CH$_2$)$_2$NH | H | colourless needlelike crystals 148–151 | 3430, 1722, 1620 | 1.16(3H, t, J=7.3Hz), 1.40(3H, t, J=7.0Hz), 1.98(1H, br.s), 2.49(2H, q, J=7.3Hz), 2.8–3.3(8H, m), 4.39 (2H, q, J=7.0Hz), 5.42(1H, s), 5.58(1H, s), 6.65(1H, d, J=7.0Hz), 8.04(1H, d, J=13.2Hz), 8.31(1H, s) |
| 42 | C$_2$H$_5$ | C$_2$H$_5$ | —N(pyrrolidinyl with CH$_3$) | H | brown needlelike crystals 132–134 | 3425, 1720, 1612 | 1.15(3H, d, J=6.2Hz), 1.16(3H, t, J=7.3Hz), 1.41(3H, t, J=7.0Hz), 1.9–2.2(1H, br.s), 2.2–2.6(3H, q-like), 2.6–3.2(4H, m), 3.3–3.6(2H, m), 4.38(2H, q, J=7.0Hz), 5.43(1H, s), 5.59(1H, s), 6.65(1H, d, J=7.0Hz), 8.04(1H, d, J=13.2Hz), 8.31(1H, s) |

Example 4

6-Fluoro-7-(4-methyl-)-1-piperazinyl)-1-(prop-1-en-2-yl)-1,4-dihydro-4-oxoquinoline-3-carboxylic acid 28 mg (0.078 mmol) of ethyl 6-fluoro-7-(4-methyl-1-piperazinyl)-1-(prop-1-en-2-yl)-1,4-dihydro-4-oxoquinoline-3-carboxylate (Compound No. 37) obtained in Example 3 was dissolved in 6 ml of aqueous ethanol (ethanol:water=5:1). 0.12 ml of 2N sodium hydroxide was added dropwise to the solution, followed by hydrolysis with heating under refluxing for 3 hours. The reaction product was neutralized with 0.2 ml of 1N hydrochloric acid, the mixture was concentrated under reduced pressure, and the residue was extracted with methanol. 24 mg of light yellow-brown crystals of 6-fluoro-7-(4-methyl-1-piperazinyl)-1-(prop-1-en-2-yl)-1,4-dihydro-4-oxoquinoline-3-carboxylic acid (Compound No. 29) was obtained by evaporating methanol.

Reference Example 4

Ethyl 1-(1-chloroprop-2-yl)-6,7-difluoro-1,4-dihydro-4-oxoquinoline-3-carboxylate 4.45 gm (14.3 mmol) of ethyl 6,7-difluoro-1,4-dihydro-1-(1-hydroxyprop-2-yl)-4-oxoquinoline-3-carboxylate and 5.10 gm (42.9 mmol) of thionyl chloride were dissolved into 130 ml of chloroform for reaction with heating under refluxing for 1 hour. After cooling, the solvent was evaporated under reduced pressure, the residue was purified by silica gel column chromatography (chloroform:methanol=100:1), and recrystallized from ethanol to obtain 3.53 gm of colorless, needlelike crystals of ethyl 1-(1-chloroprop-2-yl)-6,7-difluoro-1,4-dihydro-4-oxoquinoline-3-carboxylate:

mp: 184°–158° C.

IR (KBr): 1725, 1618, 1598, 1502 cm$^{-1}$.

$^1$H-NMR (CDCl$_3$) δ ppm: 1.42(3H, t, J=7.1Hz), 1.77(3H, d, J=6.8Hz), 3.86(2H, d, J=5.7Hz), 4.41(2H, q, J=7.1Hz), 4.6–5.1(1H, m), 7.37(1H, d, d, J=11.6Hz, 6.1Hz), 8.34(1H, d, d, J=10.3Hz, 9.0Hz), 8.56 (1H, s).

Reference Example 5

Ethyl (3S)-7-(3-aminopyrrolidinyl)-1-(1-chloroprop-2-yl)-6-fluoro-1,4-dihydro-4-oxoquinoline-3-carboxylate 660 mg (2 mmol) of ethyl 1-(1-chloroprop-2-yl)-6,7-difluoro-1,4-dihydro-4-oxoquinoline-3-carboxylate and 414 mg (4.8 mmol) of 3S-(-)-3-aminopyrrolidine were dissolved in 40 ml of acetonitrile and the mixture was heated under refluxing for 4 hours. After the reaction, the solvent was evaporated under reduced pressure and the residue was purified by silica gel column chromatography (chloroform: methanol:aqueous ammonia=300:6:1) to obtain 465 mg of light yellow crystal of ethyl (3S)-7-(3-aminopyrrolidinyl)-1-(1-chloroprop-2-yl)-6-fluoro-1,4-dihydro-4-oxoquinoline-3-carboxylate.

mp. 149°-152° C.
IR (KBr): 3415, 1712, 1625, 1512 cm$^{-1}$.
$^1$H-NMR (CDCl$_3$) δ ppm:
1.39(3H, t, J=7.0Hz), 1.70(2H, s, disappeared by D$_2$O), 1.74(3H, d, J=7.0Hz), 3.1-3.9(7H, m), 4.37(2H, q, J=7.0Hz), 8.42(1H, s).

Example 5

(3S)-7-(3-aminopyrrolidinyl)-6-fluoro-1,4-dihydro-4-oxo-1-(prop-1-en-2-yl)-quinoline-3-carboxylic acid 753 mg (1.9 mmol) of ethyl (3S)-7-(3-aminopyrrolidinyl)-6-fluoro-1,4-dihydro-4-oxoquinoline-3-carboxylate obtained in Reference Example 5 was dissolved in 50 ml of ethanol, and to this was added 320 mg (5.7 mmol) of pulverized potassium hydroxide for the reaction with heating under refluxing for 26 hours. After cooling, the reaction product was neutralized with 1 N hydrochloric acid to adjust to pH 7-8. The precipitate produced was filtrated, washed with water, air-dried, and dried under reduced pressure to obtain 597 mg of (3S)-7-(3-aminopyrrolidinyl)-6-fluoro-1,4-dihydro-4-oxo-1-(prop-1-en- 2-yl)-quinoline-3-carboxylic acid (Compound No. 43).

mp: 249°-255° C.
IR (KBr): 3375, 1720, 1625, 1502 cm$^{-1}$.
$^1$H-NMR (d$_6$-DMSO) δ ppm: 1.6-2.2(2H, m), 2.23(3H, s), 3.0-4.4(3H, br),3.2-3.8(5H, m) 5.51(1H, s), 5.71(1H, s), 6.43(1H, d, J=7.7Hz), 7.79(1H, d J=14.3Hz), 8.51(1H, s).

TEST EXAMPLE 1

Antimicrobial Activity

Antimicrobial activities agent bacteria listed in Table 4 were measured according to the MIC measurement method of The Japan Chemotherapeutic Association. Ofloxacin was used as a control. The results are shown in Table 4.

Medium: Mueller Hinton Medium
Sample dilution: A 1000 mcg/ml solution in 25% dimethyl sulfoxide was prepared. A series of solutions with various concentrations (100 mcg-0.006 mcg) were prepared by successively diluting the solution with sterilized water by a factor of ½.
Amount of inoculated bacteria: 10$^6$/ml.
Cultivation conditions: 37° C., 48 hours.
Determination: After 24 hours.

TABLE 4

| STRAINS FOR THE TEST | TEST COMPOUNDS (MIC degree: mg/ml) | |
|---|---|---|
| | Compound No. 43 | Ofloxacin |
| Gram Positive Bacteria | | |
| 1. *Bacillus subtilis* ATCC 6633 | 0.049 | 0.098 |
| 2. *Staphylococcus aureus* FDA 209P | 0.049 | 0.098 |
| 3. *Staphylococcus aureus* Terashima | 0.39 | 0.78 |
| 4. *Staphylococcus aureus* Smith | 0.049 | 0.195 |
| 5. *Staphylococcus epidermidis* ATCC 12228 | 0.39 | 0.78 |
| 6. *Sarcina lutea* ATCC 9341 | 0.78 | 3.12 |
| 7. *Streptococcus faecalis* IFO 12964 | 0.78 | 1.56 |
| 8. *Micrococcus lysodeikticus* IFO 3333 | 0.39 | 1.56 |
| Gram Negative Bacteria | | |
| 9. *Escherichia coli* O-1 | 0.098 | 0.098 |
| 10. *Escherichia coli* K-12 | 0.098 | 0.098 |
| 11. *Pseudomonas aeruginosa* IFO 13736 | 0.78 | 0.78 |
| 12. *Pseudomonas aeruginosa* P$_2$ | 0.78 | 0.78 |
| 13. *Pseudomonas aeruginosa* IFO 12582 | 3.12 | 3.12 |
| 14. *Klebsiella pneumoniae* ATCC 10031 | 0.012 | 0.012 |
| 15. *Proteus vulgaris* OXK | 0.024 | 0.024 |
| 16. *Serratia marcescens* NHL | 0.098 | 0.049 |
| Methicillin Resistant Staphylococcus | | |
| 17. M.R. *Staphylococcus aureus* 395 | 0.195 | 0.39 |
| 18. M.R. *Staphylococcus aureus* 415 | 0.195 | 0.39 |
| 19. M.R. *Staphylococcus aureus* 419 | 0.098 | 0.195 |
| 20. M.R. *Staphylococcus aureus* 420 | 0.098 | 0.195 |
| 21. M.R. *Staphylococcus aureus* 421 | 0.098 | 0.195 |

Table 4 shows that the compounds of this invention have stronger antimicrobial activity than ofloxacin, and that it is effective as an antimicrobial agent.

Industrial Applicability

The compound (I) of this invention exhibits an excellent antimicrobial activity and superior absorptivity, and efficiently utilized by living bodies, so that an antimicrobial agent comprising the same as an effective component is useful for prevention and cure of infection of mammal including human being.

What is claimed is:

1. A quinolone carboxylic acid compound of the formula (I), or a salt thereof

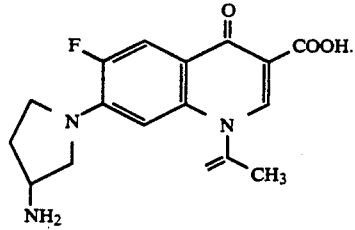

(I)

2. A quinolone carboxylic acid compound of claim 1, wherein said compound is (3S)-7-(3-aminopyrrolidinyl)-6-fluoro-1,4-dihydro-4-oxo-1-(prop-1-en-2-yl)-quinoline-3-carboxylic acid, or a salt thereof.

3. An antimicrobial composition comprising an inert carrier and an antimicrobially effective amount of a compound according to claim 1.

4. An antimicrobial composition comprising an inert carrier and an antimicrobially effective amount of a compound according to claim 2.

* * * * *